United States Patent [19]
Baltz et al.

[11] Patent Number: 5,981,281
[45] Date of Patent: Nov. 9, 1999

[54] **METHOD FOR KNOCKOUT MUTAGENESIS IN *STREPTOCOCCUS PNEUMONIAE***

[75] Inventors: Richard Henry Baltz; Jo Ann Hoskins; Patricia Jean Solenberg, all of Indianapolis; Patti Jean Treadway, Greenwood, all of Ind.

[73] Assignee: Eli Lilly and Company, Indianapolis, Ind.

[21] Appl. No.: 08/987,152

[22] Filed: Dec. 8, 1997

Related U.S. Application Data

[60] Provisional application No. 60/036,281, Dec. 13, 1996.
[51] Int. Cl.[6] .......................... C12N 15/00; C12N 15/31; C12N 15/87
[52] U.S. Cl. ...................... 435/477; 435/488; 435/252.3; 435/252.33
[58] Field of Search ............................... 435/172.3, 252.3, 435/477, 488, 252.33

[56] References Cited

U.S. PATENT DOCUMENTS 5,747,281  5/1998  Shuler et al. .......................... 435/69.1

OTHER PUBLICATIONS

Kolkman et al., J. Bacteriology 178(13):3736–3741 (1996).
Claverys et al., Gene 164:123–128 (1995).
Tao et al., Gene 120:105–110 (1992).
K. F. Chater and C. J. Bruton. "Mutational cloning in Streptomyces and the isolation of antibiotic production genes." *Gene* 26(1):67–78 (1983).

*Primary Examiner*—Johnny F. Railey, II
*Attorney, Agent, or Firm*—Thomas D. Webster

[57] ABSTRACT

Provided herein is a method to produce knockout mutations at targeted sites in the genome of *Streptococcus pneumoniae*.

1 Claim, 3 Drawing Sheets

_5,981,281_

METHOD FOR KNOCKOUT MUTAGENESIS IN STREPTOCOCCUS PNEUMONIAE

BACKGROUND OF THE INVENTION

This application claims the benefit of U.S. Provisional Application No. 60/036,281, filed Dec. 13, 1996.

This invention provides a method for producing knockout mutations in Streptococcus pneumoniae.

The recent emergence of widespread antibiotic resistance in common pathogenic bacterial species has justifiably alarmed the medical and research communities. Frequently these organisms are co-resistant to several antibacterial agents. Particularly problematic has been the rapid spread of penicillin resistance in Streptococcus pneumoniae, which frequently causes upper respiratory tract infections. Resistance to penicillin in this organism can be due to modifications of one or more of the penicillin-binding proteins (PBPs). Combating the phenomenon of increasing resistance to antibiotic agents among pathogenic organisms such as Streptococcus pneumoniae will require intensified research into the fundamental molecular biology of such organisms.

While inroads in the development of new antibiotics and new targets for antibiotic compounds have been made with a variety of microorganisms, progress has been less apparent in Streptococcus pneumoniae. In part, Streptococcus pneumoniae presents a special case because this organism is highly recombinogenic and readily takes up exogenous DNA from its surroundings. Thus, the need for new strategies and methods for developing antibacterial compounds in Streptococcus pneumoniae is pressing.

BRIEF SUMMARY OF THE INVENTION

The present invention relates to a method for targeted mutagenesis in S. pneumoniae. The method disclosed herein enables targeted mutagenesis of the S. pneumoniae genome.

In one embodiment the present invention provides a method for producing targeted knockout mutations in the S. pneumoniae chromosome.

In another embodiment, the present invention provides mutated strains of S. pneumoniae produced by the method disclosed herein.

DEFINITIONS

Figure 1:
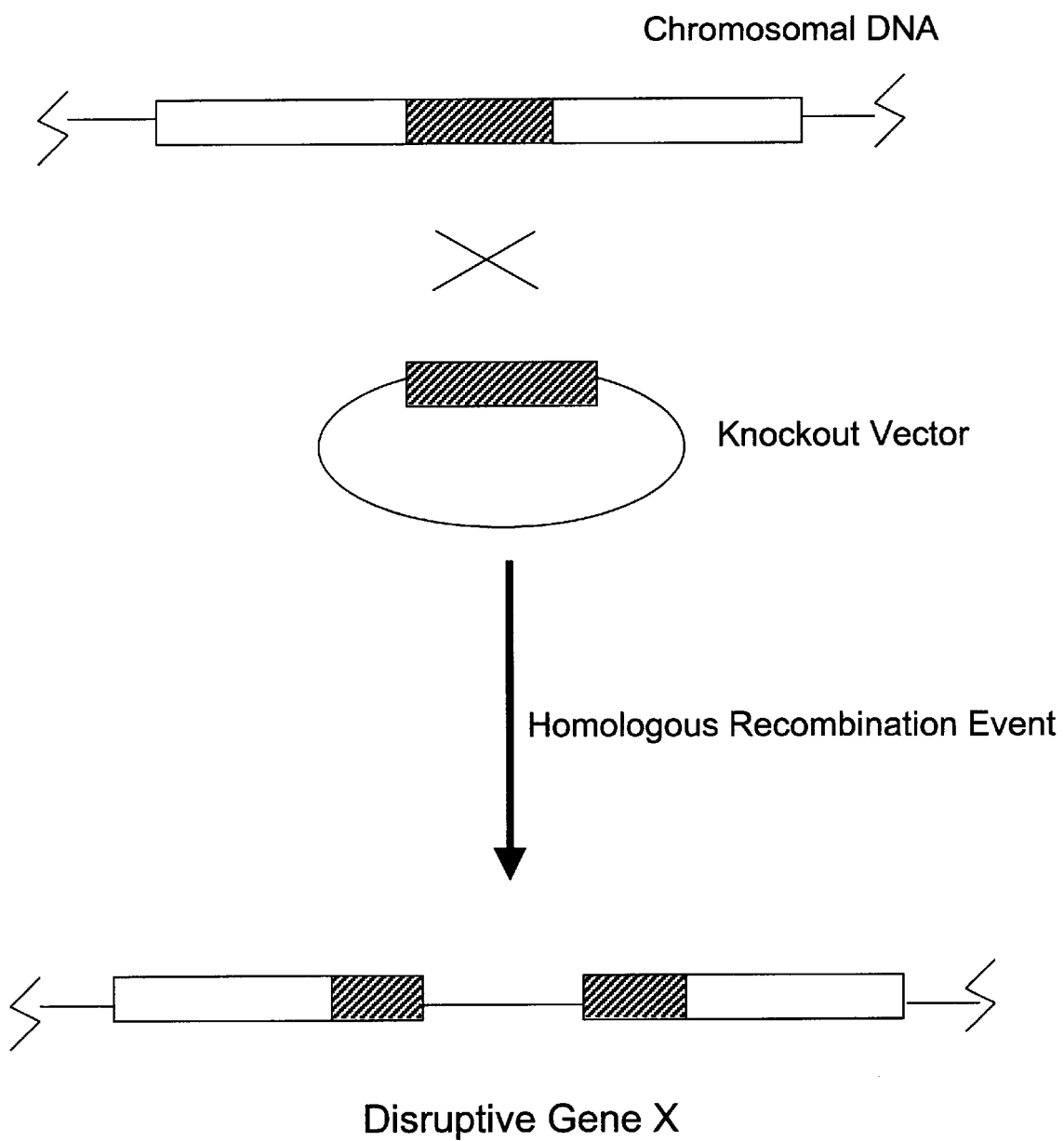
FIG. 1. Schematic of knockout method wherein a plasmid carrying a fragment of the S. pneumoniae genome is transferred by conjugation to S. pneumoniae cells, whereupon said plasmid recombines with the chromosome to produce a knockout mutation.

"Genome" refers to the full complement of chromosomal and extra-chromosomal DNA within a cell. The genome comprises the genetic blueprint for all proteins and RNAs encoded by the cell or organism.

"Essential genes" or "essential ORFs" or "essential proteins" refer to genomic information or the protein(s) or RNAs encoded therefrom which, when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Knockout mutant" or "knockout mutation" as used herein refers to an in vitro engineered disruption of native chromosomal DNA, typically within a protein coding region, such that a foreign piece of DNA conveniently but not necessarily providing a dominant selectable marker is inserted within the native sequence. A knockout mutation within a protein coding region prevents expression of the wild-type protein, which usually leads to loss of the function provided by the protein. A "knockout cassette" refers to a fragment of native chromosomal DNA having cloned therein a foreign piece of DNA that may provide a selectable marker.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Oligonucleotide" refers to a short polymeric nucleotide chain comprising from about 2 to 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

DETAILED DESCRIPTION OF THE INVENTION

The Streptococcus pneumoniae genome is estimated to contain about 2.2 million nucleotide base pairs and to comprise about 2000 to 3000 ORFs and other genes. This invention provides a method for producing targeted knockout mutations within the S. pneumoniae genome.

Production of Knockout Mutations

The invention provides a method for producing knockout mutations in the S. pneumoniae genome. Knockout mutations are useful for a variety of applications. For example, the knockout procedure disclosed herein provides a method for (1) identifying the function of a protein in the cell, (2) constructing merodiploid strains, (3) introducing foreign genes onto the S. pneumoniae chromosome, (4) construction of strains with altered regulatory properties, (5) construction of defined mutations in which a wild type genomic sequence is replaced by a mutated copy of the wild-type sequence.

Abrogating normal production of a protein is a means of perturbing the cell in a defined way. Critical biological functions can be affected by knockout mutations, and in some instances these can be determined easily by, for example, loss of viability. In other instances the phenotypic affect of a knockout mutation will require systematic screens to test for a loss in specific enzyme activities, for example, or, for changes in growth requirements.

Figure 2:
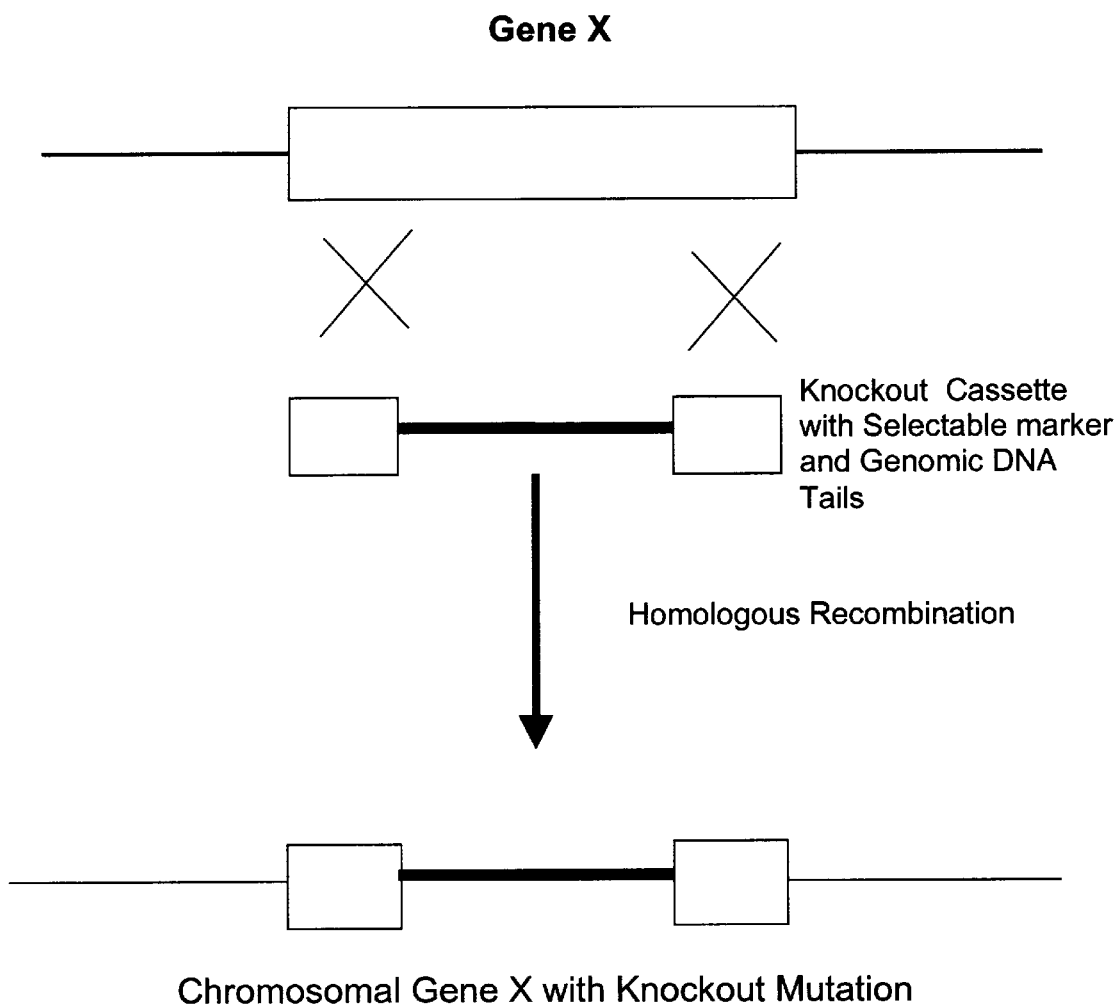
FIG. 2. Schematic of knockout mutagenesis, by transformation with a "knockout cassette".

In one embodiment "knockout mutation cassettes" are created by interrupting a fragment of genomic DNA with a foreign piece of DNA, and replacing the wild-type chromosomal copy of the sequence with the knockout cassette (See FIG. 2). In this embodiment, the knockout protocol involves cloning a foreign piece of DNA into a target DNA such that "tails" comprising the target site DNA remain at the 5' and 3' ends of the knockout cassette. The tails should be at least 50 base pairs and preferably greater than 200 to 500 base pairs for efficient recombination and/or gene conversion. For convenience, the foreign DNA cloned into the target DNA also provides a selectable marker, for example, an antibiotic resistance gene.

The knockout procedure can be carried out by mixing a knockout gene cassette with a culture of S. pneumoniae competent for DNA uptake. While S. pneumoniae is naturally transformable it is preferred that cells be rendered competent for DNA uptake by any suitable method (See e.g. LeBlanc et.al. Plasmid 28, 130–145, 1992; Pozzi et al. J. Bacteriol. 178, 6087–6090, 1996). Where the target DNA is disrupted with an antibiotic resistance gene, selection of transformants is carried out on agar plates containing suitable levels of an appropriate antibiotic. Following transformation, a fraction of cells that have taken up the knockout cassette will have undergone homologous recombination or gene conversion across the genomic DNA tails of the cassette, resulting in replacement of the wild-type genomic sequence with the knockout cassette (See FIG. 2). Knockout recombination events are easily confirmed by, for example, Southern blot hybridization, or more conveniently by PCR.

Figure 3:
FIG. 3. Plasmid pCZA342 replicates in E. coli but not in S. pneumoniae. This plasmid provides a universal cloning site for insertion of genomic DNA fragments.

In the preferred method for producing knockout mutations in S. pneumoniae, a fragment of S. pneumoniae genomic DNA (i.e. target site) disclosed herein is cloned into a suitable plasmid or other vector. The recombinant vector is introduced into E. coli by transformation and transferred from E. coli to S. pneumoniae by conjugation. The knockout vector then recombines with the S. pneumoniae chromosome across the target site to produce a disrupted genomic fragment (See FIG. 1). The target DNA can comprise any DNA sequence disclosed herein, and is easily made by the PCR using conventional techniques. A suitable cloning vector for the conjugation method has several salient features. First, the vector should replicate and be selectable in E. coli, (2) the vector should be selectable but not replicate in S. pneumoniae, and (3) the vector should be transferable from E. coli to S. pneumoniae by conjugation. A preferred cloning vector for this purpose is pCZA342 (See FIG. 3). The conjugation method of the knockout procedure is disclosed more fully in the accompanying Examples.

Skilled artisans will recognize that the knockout cassettes and the DNA segments of this invention or fragments thereof can be generated by general cloning methods. PCR amplification methods using oligonucleotide primers targeted to any suitable region of any of the sequences disclosed herein are preferred. Methods for PCR amplification are widely known in the art. See e.g. *PCR Protocols: A Guide to Method and Application*, Ed. M. Innis et al., Academic Press (1990) or U.S. Pat. No. 4,889,818, which hereby is incorporated by reference. The PCR comprises genomic DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology*, 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach*, (1984)], or phosphoramidite chemistry.

The following examples more fully describe the present invention. Those skilled in the art will recognize that the particular reagents, equipment, and procedures described are merely illustrative and are not intended to limit the present invention in any manner.

EXAMPLE 1

Construction of Direct Selection Knockout Cassette

Genomic DNA from S. pneumoniae strain R6 hex$^-$ was used as a source of DNA for PCR amplification (strain obtained from Dr. Alexander Tomasz, Rockefeller University; See S. Lacks "Mutants of *Diplococcus pneumoniae* that lack deoxyribonucleotides and other activities possibly pertinent to genetic transformation," *J. Bacteriol.* 101, 373–83, 1970). About 10 ml of bacteria were grown overnight at 37° C. in brain heart infusion broth without shaking. The cells were harvested by centrifugation, washed one time in 50 mM Tris, 50 mM EDTA, and resuspended in 300 ul of 50 mM Tris 50 mM EDTA, 100 ug/ml RNAse. Cells were lysed by the addition of 30 ul 4% deoxycholate and 30 ul 0.1% sodium dodecylsulfate with incubation at 37° C. for about 1 hour, or until the solution cleared. The solution was extracted with 0.2 ml of TE-buffered phenol and the aqueous phase transfered to a clean tube. After another phenol extraction the DNA was precipitated by adding one-tenth volume of 3M sodium acetate and 2 volumes cold ethanol. The DNA was recovered by centrifugation and resuspended in 500 ul of TE pH 8. After a reprecipitation step, the DNA pellet was resuspended in 50 ul to 100 ul of TE. About 1 ul of DNA solution was used for each PCR reaction.

Skilled artisans will recognize that within a particular set of PCR primers, one of the oligonucleotides should be derived from the coding strand of the DNA to be amplified and the other should be derived form the non-coding strand. The primers can be synthesized by the modified phosphotriester method using fully protected deoxyribonucleotide building blocks, as described, for example, in Narang et.al., *Methods in Enzymology*, 68, 90 (1980). A preferred method employs automated DNA synthesizers, such as the Applied Biosystems 394 DNA Synthesizer (850 Lincoln Centre Drive, Foster City, Calif. 94404).

The amplification reaction was performed in a DNA Thermal Cycler using a Gene Amp Kit according to the manufacturer's instructions (Perkin Elmer Cetus, Norwalk, Conn.). A thermal step program that included the following parameters was used for DNA amplification: denaturation at 94° C. for 30 seconds, annealing at 55° C. for 30 seconds, primer extension at 72° C. for two minutes, for a total of 30 cycles. Ten ul of the PCR amplification product was analyzed by agarose gel electrophoresis on a 0.8% agarose gel. A positive result was indicated by the presence of an approriately-sized band. The amplified fragment was extracted from an agarose gel and used to construct a knockout plasmid, as illustrated in Example 2 for the nanA gene.

EXAMPLE 2

Construction of a plasmid for use in Knockout Mutagenesis of nanA Gene

The S. pneumoniae nanA gene comprises 3107 base pairs and encodes the enzyme neuraminidase. The nucleotide sequence of this gene has been published (M. Camara et.al. Infection and Immunity, 62, 3688–95, 1994). Oligonucleotide primers targeting a 559 base pair region at the 5' end of nanA were synthesized to contain BamHI cloning sites. This region of nanA was amplified from genomic DNA, and the amplified DNA was gel-purified and digested with BamHI. The BamHI-digested DNA fragment was ligated into plasmid pCZA342(FIG. 3), which carries oriT, an apramycin resistance gene, and an erythromycin resistance gene. The erythromycin gene provides a selectable marker for S. pneumoniae. The resulting plasmid, pCZA342-nanA, was used to produce a knockout mutation in the nanA gene by conjugation (described in Example 3).

EXAMPLE 3

Producing a Knockout Mutation in S. pneumoniae by Conjugation

S. pneumoniae R6 hex⁻ cells from frozen stock were grown in Brain Heart Infusion broth (BHI) supplemented with 35 mM L-threonine overnight at 37° C. to an $OD_{660}$ of 0.52 to 0.58 (this cell density range provides optimal results). The cells were harvested prior to entering stationary phase.

E.coli S17-1 (obtained from Pasteur Institute, Ref. R. Simon et.al., *Bio/Technology*, 1, 784–791, 1983) was transformed by standard methods with plasmid pCAZ342-nanA (see Example 2). The transformed *E. coli* cells were grown to stationary phase in TY broth supplemented with 100 ug/ml apramycin overnight at 37° C. on a roller drum.

For conjugation, R6 and S17-1 cells, grown as described, were mixed in the following ratios: 9/1, 1/1, and 1/9, in 3 separate tubes, each containing 0.2 ml BHI broth. The mixed cells were pelleted and resuspended in the residual growth medium. Samples from each tube were spotted onto the surface of a chocolate II agar plate (BBL, Becton-Dickson) and incubated overnight at 37° C. Cells that grew at each spot were scraped from the plate, and resuspended in 0.5 ml BHI broth. The resuspended cells were plated in Nutrient Broth soft agar, onto chocolate agar plates supplemented with 0.3 ug/ml erythromycin and 30 ug/ml nalidixic acid. Drug-resistant colonies appeared after an overnight incubation at 37° C.

Drug-resistant colonies were tested for knockout gene replacement first by Southern blot hybridization to demonstrate that the nanA bearing plasmid had integrated into the *S. pneumoniae* chromosome. The Southern-blot tests demonstrated disruption of the native chromosomal sequence, and more importantly replacement of the wild-type nanA sequence by pCZA343-nanA. Moreover, neuraminidase enzyme activity was absent in extracts prepared from the exconjugants, as expected following inactivation of nanA.

We claim:

1. A method for producing a targeted knockout mutation in *Streptococcus pneumoniae* comprising the steps of:

a. transforming *E. coli* with a plasmid that carries a *S. pneumoniae* genomic DNA fragment;

b. conjugating a transformant from step (a) with *S. pneumoniae*;

c. selecting exconjugants from step (b) by any suitable means; and d. verifying a knockout mutation by any suitable means.

* * * * *